（12) United States Patent
Jenkins et al.

(10) Patent No.: US 6,908,434 B1
(45) Date of Patent: Jun. 21, 2005

(54) ULTRASOUND IMAGING CATHETER ISOLATION SYSTEM WITH TEMPERATURE SENSOR

(75) Inventors: David Jenkins, Flanders, NJ (US); Simcha Borovsky, Fair Lawn, NJ (US)

(73) Assignee: EP MedSystems, Inc., West Berlin, NJ (US)

( * ) Notice: Subject to any disclaimer, the term of this patent is extended or adjusted under 35 U.S.C. 154(b) by 0 days.

(21) Appl. No.: 10/345,806

(22) Filed: Jan. 16, 2003

Related U.S. Application Data

(60) Provisional application No. 60/349,060, filed on Jan. 16, 2002.

(51) Int. Cl.[7] ................................................ A61B 8/14
(52) U.S. Cl. ..................................................... 600/466
(58) Field of Search ............................... 600/437–472; 367/7, 11, 130, 138, 117, 121, 122; 607/101, 607/113; 310/314–317; 128/916; 73/625, 73/626; 604/22

(56) References Cited

U.S. PATENT DOCUMENTS

| 4,319,580 A | * | 3/1982 | Colley et al. ................ 600/453 |
| 6,540,677 B1 | * | 4/2003 | Angelsen et al. ........... 600/437 |

* cited by examiner

Primary Examiner—Ali Imam
(74) Attorney, Agent, or Firm—Norman E. Lehrer

(57) ABSTRACT

An ultrasonic imaging catheter is disclosed that includes a thermistor mounted on the catheter in the vicinity of the ultrasound transducer for monitoring the temperature in the vicinity thereof. The electrical signal from the thermistor can be used to control the output of the ultrasound transducer to thereby control the temperature of the same. In a further aspect of the invention, an isolation box is provided that is external to the ultrasound machine itself and is connected to the same by a cable. Ideally, the isolation box which houses a sufficient number of isolation transformers, is small, so it can be placed easily on or near the patient's bed.

11 Claims, 1 Drawing Sheet

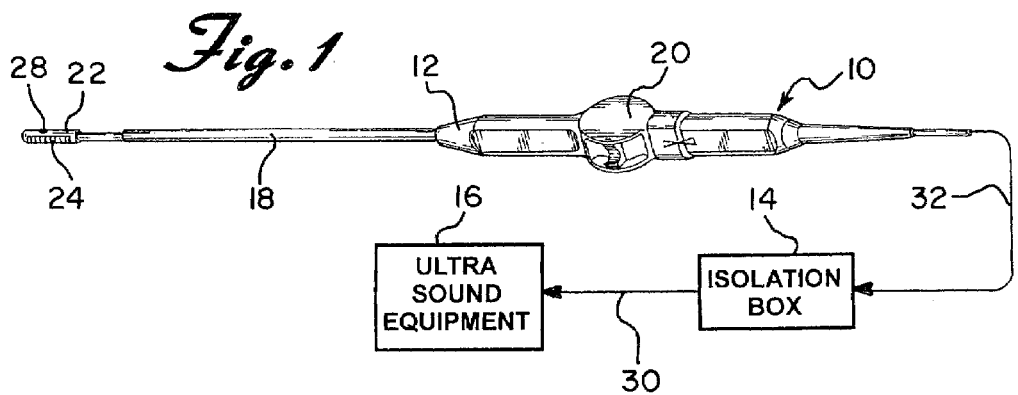
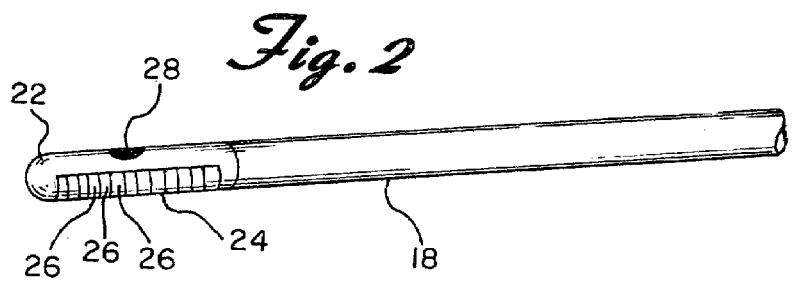
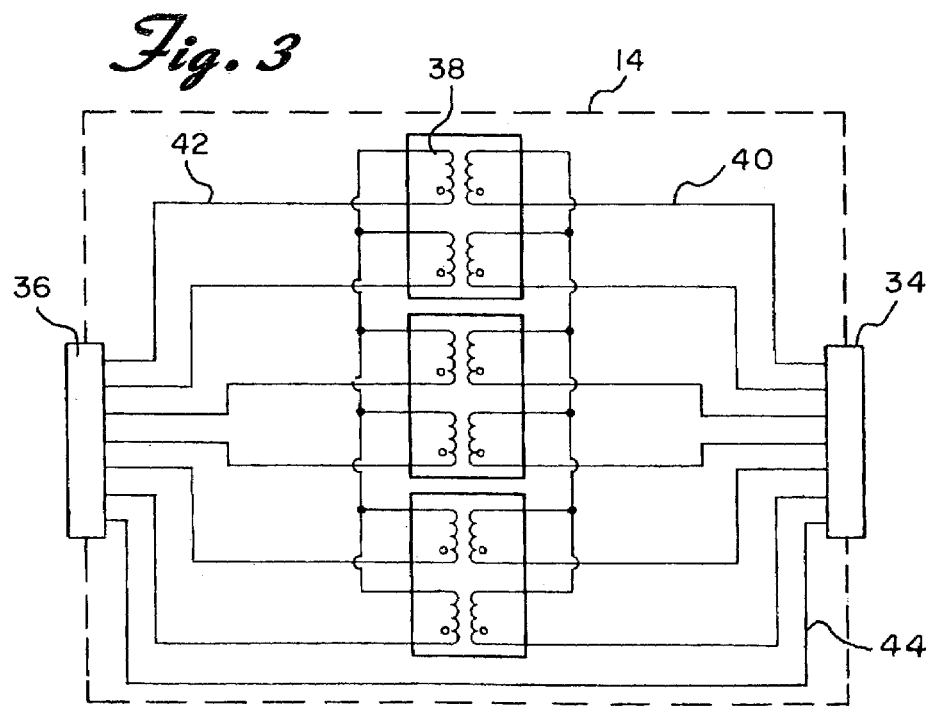

ULTRASOUND IMAGING CATHETER ISOLATION SYSTEM WITH TEMPERATURE SENSOR

CROSS-REFERENCE TO RELATED APPLICATION

This application claims the benefit of U.S. Provisional Patent Application Ser. No. 60/349,060, filed Jan. 16, 2002.

FIELD OF THE INVENTION

The present invention is directed toward improvements in ultrasound catheters and more particularly toward an ultrasound catheter that includes a temperature monitoring system carried at least in part by the catheter for preventing the overheating of the same. The invention also includes an isolation box external to the ultrasound machine that can be placed easily on or near a patient bed and connected to the ultrasound machine by a reusable connector cable.

BACKGROUND OF THE INVENTION

Recent progress in the treatment of certain diseases of the heart may require better visualization than is afforded by what has been the standard form of visualization, or imaging of the heart. The standard form of imaging has been x-ray, or x-ray fluoroscopy which has a number of disadvantages. Imagining by use of ultrasound offers a number of advantages, primarily surrounding better anatomical images. Recent progress in economically reducing the size of connecting cables to an ultrasound transducer allows for the cabling to be put through a small plastic tube, or catheter, so the ultrasound probe can be inserted percutaneously into the body. Closer proximity to the heart can provide better visualization, with higher resolution, of the desired anatomy. See, for example, U.S. Pat. No. 5,713,363 and Pending U.S. application Ser. No. 09/263,755 filed Mar. 5, 1999 assigned to the Assignee of the present application.

An ultrasound transducer is a piezoelectric material that essentially converts electrical voltage to a sound wave. In intracardiac imaging, the transducer would be placed at the distal top of a catheter, and the transducer then could be inside the heart, to send and receive the sound waves. Used with higher power, such as that used with color doppler imaging, and for a lengthy period of time, it is possible that the transducer, and hence, catheter tip, may heat up, and such heat may be well above a safe body temperature. While computer software can be used to regulate the amount of power put into the catheter, a software malfunction could result in too much power being delivered. It is, therefore, desirable to have a safety cut-off mechanism or other control to avoid such a problem.

Actual temperature monitoring near the top or tip of the catheter is most desirable, with feedback to the computer, with an automatic warning or shut down based upon some upper pre-determined temperature limit. The safety standard set out in the U.S. FDA guidelines is 430° C. although this may vary depending on the environment in which the catheter is being used.

Another problem with ultrasound imaging with a catheter, especially with a multi element array, is that the cabling from the ultrasound machine to the catheter, and from the catheter proximal connector to the catheter transducer housed at the distal tip, is expensive. A first solution to keep the expense low, is to move the ultrasound machine next to the bed, and plug the relatively short catheter directly to the ultrasound machine. This is impractical, as most catheter rooms are sterile or semi-sterile environments, and the machine may have to be some distance for the patient bedside. Thus, a connecting cable which is reusable (and probable non-sterile) is desirable, as opposed to the catheter itself, which is sterile and usually not re-usable. It would be most desirable if this connecting cable could be used as a universal cable in that it could be used with many ultrasound machines. Many ultrasound machines have a standard 200 pin ZIF connector, but most ultrasound machines do not have patient isolation built in to the degree necessary for percutaneous catheter use.

SUMMARY OF THE INVENTION

The present invention is designed to overcome the deficiencies of the prior art described above. According to one aspect of the invention, the heat safety issue is addressed by monitoring the temperature in the vicinity of the ultrasound transducer with a thermistor. While thermistors have been proposed for use with catheters for monitoring the temperature of an ablation electrode or for use in thermal dilution measurements to compute cardiac output, no one, to Applicants' knowledge, has used a thermistor for the safety elements of ultrasound imaging.

A further object of the present invention is to provide a connector cable with an isolation means that is external to the ultrasound machine itself. Ideally, the isolation box which houses a sufficient number of isolation transformers, is small, so it can be placed easily on or near the patient's bed.

Other objects and advantages of the invention will be apparent from the following description when taken with the drawings showing Applicants' presently preferred embodiments thereof.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

FIG. 1 is representation of a catheter employing the present invention with the isolation system shown schematically;

FIG. 2 is a detailed view of the end of the catheter shown in FIG. 1 illustrating the ultrasound transducer and the thermistor, and FIG. 3 is a schematic representation of the isolation circuit of FIG. 1.

DETAILED DESCRIPTION OF THE PREFERRED EMBODIMENT

Referring now to the drawings in detail wherein like reference numerals have been used throughout the various figures to designate like elements, there is shown in FIG. 1 a ultrasound imaging catheter isolation system with temperature sensor in accordance with the principles of the present invention and designated generally as 10. The system 10 is comprised essentially of three parts: an ultrasound catheter with transducer assembly 12, an isolation box 14 and the ultrasound equipment 16.

In many respects, the catheter and transducer assembly 12 is constructed in a conventional manner similar, for example, to the ultrasound catheter described in the aboveidentified application Ser. No. 09/263,755 filed Mar. 5, 1999, the entire content of said application being incorporated herein by reference. It should be noted, however, that the present invention is not limited to the specific catheter assembly disclosed in the prior referenced application as the invention is applicable to various catheters designed for intravascular/intracardiac echocardiography and for other physiological uses.

The catheter assembly 12 includes an elongated catheter in the form of a tube 18. The proximal end of the tube 18 is connected to a handle mechanism 20 which includes means for steering the ultrasound probe 22 mounted at the distal end of the catheter tube 18. As is well known in the art, the ultrasound probe 22 includes an ultrasound transducer assembly 24 which is comprised of a number of ultrasonic transducer elements 26. Although only 12 or so transducer elements 26 are shown in FIG. 2, substantially any number of transducer elements may be employed as described in the prior application discussed above.

Mounted on the reverse side of the ultrasound transducer probe 22 is a thermistor 28. The thermistor 28 is preferably embedded within the probe 22 so as to provide a smooth outer surface on the probe. The exact location of the thermistor 28 is not critical. However, it must be in such a position so as to be able to sense the temperature of the tissue in the vicinity of the probe and/or the temperature of the probe itself without interfering with the operation of the same. Furthermore, while the invention has been described with specific reference to a thermistor 28, it should be readily apparent that other similar types of devices may also be employed which are capable of sensing temperature. The electrical wires leading from the thermistor 28 pass through the center of the catheter body 18 to the exterior of the body in substantially the same manner as the numerous wires connected to the ultrasonic transducer elements 26.

The ultrasound equipment 16 illustrated in FIG. 1 is a conventional ultrasound machine which operates in a manner well known in the art. This equipment 16 may be located away from a patient's bed outside of the sterile area. The isolation box 14, however, is intended to be placed on or near a patient's bed within the sterile area and a cable 30 connects the two together.

The cable 32 from the catheter assembly 12 carries a plug at the end thereof that plugs into the isolation box 14. Since the isolation box is relatively small and is located on or near the patient's bed, the cable 32 can also be relatively short, thereby reducing the cost of the same. The cable 32 carries all of the leads from the ultrasonic transducers 26, the leads from the thermistor 28 and any other leads that may be used in connection with the catheter assembly 12. For example, the catheter assembly 12 may carry other electrodes at or near the tip thereof or elsewhere along the catheter body 18 for various other purposes.

The isolation box 14 preferably has an input connector or socket 34 for connection to the cable 32 and an output socket or connector 36 for connection to the cable 30 that leads to the ultrasound equipment 16. These are conventional sockets or connectors well known in the art.

Within the isolation box 14 are a plurality of isolation transformers 38. In order to keep the isolation box as small as possible, very small transformers 38 are utilized as a significant number of them must be mounted within the box 14. There is one isolation transformer 38 for each of the ultrasonic transducer elements 26. Thus, if there are 64 transducer elements 26, an equal number i.e., 64 transformers are required. One transformer particularly useful with the present invention is a wide band isolation transformer sold by Rhombus Industries Inc. of Huntington, Calif. as Rhombus Model No. T-1113.

One side of each transformer 38 is connected by leads 40 to the socket or connector 34 so as to be connected to the transducer assembly 12 by way of the cable 32. Similar leads 42 connect the opposite side of each transformer 38 to the socket or connector 36 for ultimate connection to the ultrasound equipment 16 through the cable 30. Other leads such as shown at 44 may pass directly through the isolation box 14 from connector 34 to connector 36 without being connected to an isolation transformer if the same is desired. For example, the lead from the thermistor 28 may not pass through an isolation transformer 38 but may be connected directly to the ultrasound equipment 16 by passing through the isolation box 14. As should be readily apparent to those skilled in the art, appropriate circuitry may be located either in isolation box 14 or the ultrasound equipment 16 or elsewhere for interpreting the signal from the thermistor 28 for controlling the ultrasound equipment in response thereto.

The present invention may be embodied in other specific forms without departing from the spirit or essential attributes thereof and accordingly, reference should be made to the appended claims rather than to the foregoing specification as indicating the scope of the invention.

We claim:

1. An ultrasound imaging catheter system comprising:
   an elongated catheter body having a proximal end and a distal end and at least one lumen within said body that extends substantially throughout the length thereof;
   an ultrasound transducer assembly carried by said catheter body adjacent said distal end for use in imaging;
   ultrasound equipment located at a position remote from said catheter body for controlling said ultrasound transducer assembly;
   electrical wires connected between said ultrasound transducer assembly and said ultrasound equipment;
   means carried by said catheter body adjacent said distal end for sensing temperature and means electrically connecting said temperature sensing means to said ultrasound equipment and means responsive to the temperature sensing means for controlling said ultrasound equipment.

2. The ultrasound imaging catheter system as claimed in claim 1 wherein said temperature sensing means is a thermistor.

3. The ultrasound imaging catheter system as claimed in claim 1 wherein said ultrasound transducer assembly is comprised of a plurality of transducer elements.

4. The ultrasound imaging catheter system as claimed in claim 3 further including an isolation circuit between said ultrasound transducer assembly and said ultrasound equipment.

5. The ultrasound imaging catheter system as claimed in claim 4 wherein said isolation circuit includes a plurality of transformers.

6. The ultrasound imaging catheter system as claimed in claim 5 wherein the number of transformers is equal to the number of transducer elements.

7. An ultrasound imaging catheter system comprising:
   an elongated catheter body having a proximal end and a distal end and at least one lumen within said body that extends substantially throughout the length thereof;
   an ultrasound transducer assembly carried by said catheter body adjacent said distal end for use in imaging;

ultrasound equipment located at a position remote from said catheter body for controlling said ultrasound transducer assembly;

electrical wires connected between said ultrasound transducer assembly and said ultrasound equipment; and an isolation circuit including a plurality of transformers located between said ultrasound transducer assembly and said ultrasound equipment.

8. The ultrasound imaging catheter system as claimed in claim 7 wherein said ultrasound transducer assembly is comprised of a plurality of transducer elements.

9. The ultrasound imaging catheter system as claimed in claim 7 wherein the number of transformers is equal to the number of transducer elements.

10. The ultrasound imaging catheter system as claimed in claim 7 further including means carried by said catheter body adjacent said distal end for sensing temperature and means electrically connecting said temperature sensing means to said ultrasound equipment and means responsive to the temperature sensing means for controlling said ultrasound equipment.

11. The ultrasound imaging catheter system as claimed in claim 10 wherein said temperature sensing means is a thermistor.

* * * * *